US010278924B2

(12) United States Patent
Folger et al.

(10) Patent No.: US 10,278,924 B2
(45) Date of Patent: *May 7, 2019

(54) LOW CONCENTRATION MELOXICAM TABLETS

(71) Applicant: Boehringer Ingelheim Vetmedica GmbH, Ingelheim am Rhein (DE)

(72) Inventors: Martin A. Folger, Ingelheim am Rhein (DE); Stefan Lehner, Wiesbaden (DE); Horst Schmitt, Nieder-Hilbersheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,377

(22) Filed: Sep. 11, 2017

(65) Prior Publication Data
US 2017/0367983 A1    Dec. 28, 2017

Related U.S. Application Data

(63) Continuation of application No. 13/093,886, filed on Apr. 26, 2011, now Pat. No. 9,795,568.

(30) Foreign Application Priority Data

May 5, 2010    (DE) .................. 101 62 015

(51) Int. Cl.
*A61K 9/20* (2006.01)
*A61K 9/00* (2006.01)
*A61K 31/5415* (2006.01)

(52) U.S. Cl.
CPC .......... *A61K 9/2072* (2013.01); *A61K 9/0056* (2013.01); *A61K 9/2095* (2013.01); *A61K 31/5415* (2013.01)

(58) Field of Classification Search
None
See application file for complete search history.

(56) References Cited

U.S. PATENT DOCUMENTS

| 4,482,554 | A | 11/1984 | Gebhardt et al. |
| 4,687,662 | A | 8/1987 | Schobel |
| 4,702,919 | A | 10/1987 | Kitamori et al. |
| 4,748,174 | A | 5/1988 | Veronesi |
| 5,026,560 | A | 6/1991 | Makino et al. |
| 5,283,065 | A | 2/1994 | Doyon et al. |
| 5,464,632 | A | 11/1995 | Cousin et al. |
| 5,489,439 | A | 2/1996 | Bola |
| 5,654,003 | A | 8/1997 | Fuisz et al. |
| 6,183,779 | B1 | 2/2001 | Ouali et al. |
| 6,284,269 | B1 | 9/2001 | Struengmann et al. |
| 6,599,529 | B1 | 7/2003 | Skinhøj et al. |
| 6,869,948 | B1 | 3/2005 | Bock et al. |
| 8,337,892 | B1 | 12/2012 | Couaraze et al. |
| 8,920,820 | B2 | 12/2014 | Folger et al. |
| 9,795,568 | B2 * | 10/2017 | Folger .................. A61K 9/2072 |
| 9,943,486 | B2 * | 4/2018 | Folger .................. A61K 9/2072 |
| 2002/0035107 | A1 | 3/2002 | Henke et al. |
| 2002/0068088 | A1 | 6/2002 | Gruber |
| 2002/0106345 | A1 | 8/2002 | Uhrich et al. |
| 2002/0131998 | A1 | 9/2002 | Martani |
| 2002/0169212 | A1 | 11/2002 | Stroble et al. |
| 2002/0187187 | A1 | 12/2002 | Ohki et al. |
| 2003/0109701 | A1 | 6/2003 | Coppi et al. |
| 2003/0119825 | A1 | 6/2003 | Folger et al. |
| 2004/0170687 | A1 | 9/2004 | Hurd et al. |
| 2004/0171611 | A1 | 9/2004 | Trummlitz et al. |
| 2004/0180092 | A1 | 9/2004 | Henke et al. |
| 2004/0204413 | A1 | 10/2004 | Faour et al. |
| 2004/0234596 | A1 | 11/2004 | Ohki et al. |
| 2005/0038018 | A1 | 2/2005 | Kanbe et al. |
| 2005/0245510 | A1 | 11/2005 | Friton et al. |
| 2006/0079516 | A1 | 4/2006 | Henke et al. |
| 2007/0077296 | A1 | 4/2007 | Folger et al. |
| 2008/0064759 | A1 | 3/2008 | Stamm et al. |
| 2008/0132493 | A1 | 6/2008 | Folger et al. |
| 2010/0015184 | A1 | 1/2010 | Tuel |
| 2011/0275618 | A1 | 11/2011 | Folger et al. |
| 2013/0178467 | A1 | 7/2013 | Henke et al. |
| 2014/0066440 | A1 | 3/2014 | Folger et al. |
| 2014/0113893 | A1 | 4/2014 | Folger et al. |

(Continued)

FOREIGN PATENT DOCUMENTS

| AU | 673675 B2 | 11/1996 |
| CA | 2326517 A1 | 10/1999 |

(Continued)

OTHER PUBLICATIONS

"Determining Factors for Particle Size of a Table Formulation". Techceuticals Blog, Mar. 9, 2009, 2 pages. Accessed at [http://techceuticals.com/blog/?tag=particle-size on Oct. 1, 2015.].
Abstract in English for IT1251650, 1995.
Abstract in English of JP2007197357, 2007.
Bi et al., "Evaluation of Rapidly Disintegrating Tablets Prepared by a Direct Compression Method". Drug Development and Industrial Pharmacy, vol. 25, No. 5, 1999, pp. 571-581.
International Search Report and Written Opinion for PCT/EP2011/056610 dated Jan. 26, 2012.
Lascelles et al., "Nonsteroidal anti-inflammatory drugs in cats: a review". Veterinary Annesthesia and Analgesia, 2007, pp. 1-23.
Lieberman et al., "Tablet Formulation and Design" in Pharmaceutical Dosage Forms: Tablets, vol. 1, Second Edition, Marcel Dekker, Inc., New York, New York, 1989, pp. 105-108.

(Continued)

*Primary Examiner* — Jeffrey S Lundgren
*Assistant Examiner* — William Y Lee
(74) *Attorney, Agent, or Firm* — Judy Jarecki-Black

(57) ABSTRACT

Described herein is a solid tablet that is directly-compressed of powder, including meloxicam and one or more excipients which are homogenously dispersed within the tablet that can be broken into two, three or four units with each unit containing equal amounts of the active ingredient, meloxicam.

17 Claims, 2 Drawing Sheets

(56) References Cited

U.S. PATENT DOCUMENTS

| | | |
|---|---|---|
| 2014/0332438 A1 | 11/2014 | Henke et al. |
| 2015/0051198 A1 | 2/2015 | Folger et al. |
| 2017/0035885 A1 | 2/2017 | Idzik et al. |

FOREIGN PATENT DOCUMENTS

| | | | |
|---|---|---|---|
| CA | 2503396 | A1 | 5/2004 |
| CN | 1187356 | A | 7/1998 |
| CN | 1546033 | A | 11/2004 |
| EP | 0127400 | A2 | 12/1984 |
| GB | 2455875 | A | 6/2009 |
| IT | 1251650 | B | 5/1995 |
| JP | H0912426 | A | 1/1997 |
| JP | 2007197357 | A | 8/2007 |
| WO | 199301814 | A1 | 2/1993 |
| WO | 1999009988 | A1 | 3/1999 |
| WO | 1999012524 | A1 | 3/1999 |
| WO | 1999055320 | A1 | 11/1999 |
| WO | 2000015195 | A1 | 3/2000 |
| WO | 2002085331 | A1 | 10/2002 |
| WO | 2004037264 | A1 | 5/2004 |
| WO | 2005002542 | A2 | 1/2005 |
| WO | 2006015942 | A1 | 2/2006 |
| WO | 2007039417 | A1 | 4/2007 |
| WO | 2011138197 | A2 | 11/2011 |

OTHER PUBLICATIONS

Luger et al., "Structure and physicochemical properties of meloxicam, a new NSAID". European Journal of Pharmaceutical Sciences, vol. 5, 1996, pp. 175-187.

Medina, Joe, "Section XXIV—Principles of Compounding". Tech Lectures for the Pharmacy Technician, 2008, 12 pages.

Nash et al., "A Relationship Between Screen Opening and Mesh Size for Standard Sieves"., Pharmaceutical Development and Technology, vol. 2, No. 2, 1997, pp. 185-186.

Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.

Noble et al., "Meloxicam". Drugs, vol. 51, No. 3, Mar. 1996, pp. 424-430.

Rantanen et al., "Process Analysis of Fluidized Bed Granulation". AAPS PharmsciTech, vol. 2, No. 4, Article 21, 2001, 8 pages.

Robson et al., "Intrinsic acute renal failure (ARF) associated with non-steroidal anti-inflammatory drug (NSAId) use in juvenile cats undergoing routine desexing-16 cases 1998-2005". May 2006, Journal of Veterinary Internal Medicine, vol. 20, No. 3, Abst. 109, p. 740.

Sharma et al., "Adsorption of Meloxican on Porous Calcium Silicate: Characterization and Tablet Formulation". AAPS PharmSciTech, vol. 6, No. 4, Article 76, 2005, pp. E618-E625.

Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.

Swamy et al., "Orodispersible tablets of meloxicam using disintegrant blends for improved efficacy"., Indian Journal of Pharmaceutical Science, vol. 69, No. 6, 2007, pp. 836-840. [Accessed at http://ijpsonline.com/article.asp?issn=0250-474X;year=2007;volume=69;issue=6;spa . . . on Jun. 16, 2013].

Wan et al., "Incorporation and distribution of a low dose drug in granules". International Journal of Pharmaceutics, vol. 88, 1992, pp. 159-163.

Yamashita et al., "Effects of Carprofen and Meloxicam with or without Butorphanol on the Minimum Alveolar Concentration of Sevoflurane in Dogs". The Journal of Veterinary Medical Science, Jan. 2008, pp. 29-35. [Accessed at https://www.jstage.jst.go.jp/article/jvms/70/1/70_1_20/_pdf on Mar. 5, 2014].

Parikh, D. "Chapter 1. Introduction", Handbook of Pharmaceutical Granulation Technology, Nov. 24, 2009, pp. 1-5, Chapman and Hall/CRC, Boca Raton, FL.

* cited by examiner ca. 14.00 mm ca. 16.00 mm

LOW CONCENTRATION MELOXICAM TABLETS

CROSS REFERENCE TO RELATED APPLICATIONS

This application is a continuation of, and claims benefit of, U.S. patent application Ser. No. 13/093,886, filed Apr. 26, 2011, now U.S. Pat. No. 9,795,568, which claims priority to German Application No. 10162015.1, filed May 5, 2010.

FIELD OF THE INVENTION

The present invention is directed towards a novel oral application form comprising a divisible meloxicam tablet and its production method.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is a non-steroidal-anti-inflammatory drug NSAID of the oxicam family. These types of drugs inhibit the enzyme prostaglandin H2 synthase, also called cyclooxygenase or COX. Meloxicam has anti-inflammatory, antipyretic and analgesic properties.

Meloxicam and its sodium and meglumine salts are described in EP0002482 (entirely incorporated by reference). The active ingredient alone has a low water solubility as shown in EP0945134 (entirely incorporated by reference) that also discloses the pH dependent solubility of meloxicam and its salts. There are many different application forms of meloxicam including a solution (EP1299107), a suspension (EP1066029), water-soluble granules (EP1558262), tablets made of either granules containing meloxicam (EP1942902) or of directly compressed powder mixtures (EP1385483 and GB2455875), all entirely incorporated by reference.

The objective of the present invention is to develop a readily accepted, chewable solid meloxicam tablet allowing precise dosage administration of meloxicam, even in low concentrations.

DESCRIPTION OF THE INVENTION

Figure 1A:
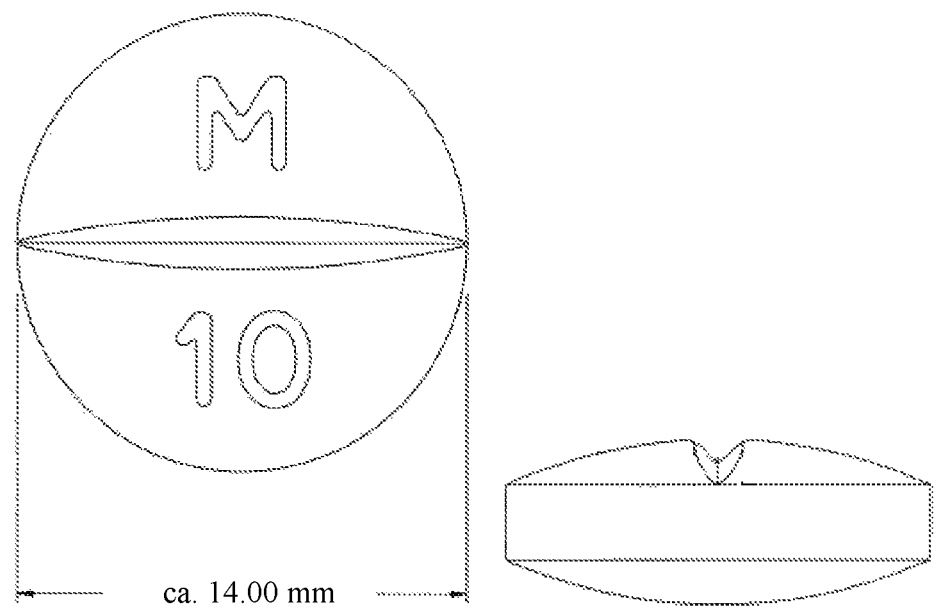
FIG. 1A: Tablet shape and dimensions of 1 mg meloxicam tablets.

Surprisingly, it has been found that such a readily accepted, chewable solid meloxicam tablet allowing precise administration of meloxicam even for exceptionally low concentrations may be prepared by the method of the current invention which is performed by direct compression of powders without any granulation step.

The tablet is administered to companion animals such as feline and canine, preferably canine, with a various body weights, including but not limited to, 1kg to 70 kg, 1 kg to 60 kg, 1 kg to 50 kg, 1 kg to 40 kg, 1 kg to 30 kg, 1 kg to 20 kg, or 1 kg to 10 kg. The tablet is administered to animals suffering from, for example, inflammation and pain in both acute and chronic musculoskeletal disorders, in order to treat or alleviate such disorders. Other indications include locomoter disorders, lameness, respiratory diseases, and pain such as postoperative pain, fever and inflammation.

The invention relates to a solid tablet that is directly-compressed of powder, comprising meloxicam or a pharmaceutically acceptable salt thereof and one or more excipients, characterized in that the tablets may be broken into two, three or four units with each unit containing equal amounts of the active ingredient. A tablet is characterized in that meloxicam is homogenously dispersed within the tablet. In another embodiment, the invention relates to a solid tablet that is directly-compressed of powder, comprising meloxicam or a pharmaceutically acceptable salt thereof and at least one excipient which is preferably homogenously dispersed within the tablet that may be broken into two, three and/or four units, preferably two or four, more preferably two, with each unit containing equal amounts of the active ingredient. The tablet contains excipients, including but not limited to, fillers/disintegrants, pH adjusters, colorants, flow regulators, lubricants, flavors and mixtures thereof.

At least one of the excipients may be a filler/disintegrant, including but not limited to, starch (such as, but not limited to, maize starch), microcrystalline cellulose, calcium phosphate, lactose, maltodextrin mannitol, sorbitol, cross-linked polyvinyl pyrrolidone, sodium carboxymethyl cellulose, and mixtures thereof, preferably starch and microcrystalline cellulose. When starch is the filler/disintegrant, then the concentration is preferably in the range of 150 mg to 450 mg per tablet, preferably 150 to 300 mg, 160 to 290 mg, 170 to 280 mg, 170 to 270 mg, 180 to 260 mg, 170 to 250 mg, 190 to 240 mg, 200 to 240 mg, 210 to 240 mg, 220 to 240 mg or 230 to 240 mg per tablet, more preferably about 235.0 mg per tablet, which is especially preferred in the tablet containing 1 mg meloxicam.

Another preferred concentration is preferably 200 to 450 mg, 210 to 440 mg, 220 to 430 mg, 230 to 420 mg, 240 to 410 mg, 250 to 400 mg, 260 to 390 mg, 270 to 380 mg, 280 to 370 mg, 290 to 360 mg, 300 to 360 mg, 310 to 360 mg, 320 to 360 mg, 330 to 360 mg, 340 to 360 mg or 350 to 360 mg per tablet, and more preferably about 351.5 mg per tablet, of which about 351.5 mg per tablet is especially preferred in the tablet containing 2.5 mg meloxicam per tablet.

A second filler/disintegrant may be included in the solid tablet or formulation and may have a concentration of preferably 300 to 800 mg per tablet, more preferably 300 to 600 mg, 300 to 500 mg, or 400 to 500 mg per tablet, and most preferably about 400 mg per tablet, which is especially preferred in the tablet containing 1 mg meloxicam. Another preferred concentration is preferably 400 to 800 mg, 500 to 700 mg, 500 to 600 mg per tablet or about 600 mg per tablet, of which about 600 mg per tablet is especially preferred in the tablet containing 2.5 mg meloxicam per tablet.

Coloring agents or colorants may also be used in the present invention. Colorants that are preferably used in the tablet are ferric oxide brown and/or ferric oxide yellow, more preferred is a mixture of ferric oxide brown and ferric oxide yellow. The concentration of each coloring agent is in the range from 2 to 8 mg per tablet, a preferred concentration is in the ranges of 3 to 5 mg per tablet, 3 to 4 mg per tablet or 3.2 mg per tablet, the 3.2 mg amount is especially preferred in the tablet containing 1 mg meloxicam. Another preferred concentration is in the range of 3 to 8 mg per tablet, 4 to 6 mg per tablet, 3 to 5 mg per tablet or 4.8 mg per tablet, which is especially preferred in the tablet containing 2.5 mg meloxicam per tablet.

The tablet may contain a pH adjuster, including but not limited to, tartaric acid, maleic acid, sodium citrate dihydrate, or mixtures thereof, and more preferably sodium citrate dihydrate. The concentration of a pH adjuster is preferably in the range from 50 mg to 150 mg; preferred concentrations of the pH adjuster include 50 to 100 mg, 50 to 90 mg, 50 to 80 mg, 50 to 70 mg, 60 to 90 mg, 60 to 80 mg or 60 to 70 mg per tablet, more preferred is about 65.6 mg per tablet in the tablet containing 1 mg meloxicam. Another preferred concentration is in the range of 75 to 150 mg, 85 to 140 mg, 85 to 130 mg, 85 to 120 mg, 85 to 110 mg, 85 to 100 mg, 90 to 150 mg, 90 to 140 mg, 90 to 130 mg, 90 to 120 mg, 90 to 110 mg, 90 to 100 mg per tablet or about 98.4 mg per tablet, which is especially preferred in the tablet containing 2.5 mg meloxicam per tablet.

The tablet may also contain a flow regulator, which may include, but is not limited to talc, anhydrous silicon dioxide, or mixtures thereof, and preferably anhydrous silicon dioxide. The preferred concentration of a flow regulator is in the range from 2 to 8 mg, preferred concentrations of the flow regulator include 2 to 6 mg, 3 to 6 mg, 3 to 5 mg, 3 to 4 mg, 2 to 5 mg or 2 to 4 mg per tablet and more preferred of about 4 mg, of which about 4 mg is especially preferred in the tablet containing 1 mg meloxicam. Another preferred concentration includes 4 to 8 mg, 5 to 8 mg, 6 to 8 mg, 6 to 7 mg, 5 to 7 mg, 4 to 7 mg, 4 to 6 mg, 5 to 6 mg per tablet, and about 6 mg per tablet, of which about 6 mg per tablet is especially preferred in the tablet containing 2.5 mg meloxicam per tablet.

The tablet may also further contain lubricants including macrogols (polyethylene glycol), stearic acid, aluminium stearate, calcium arachidate (also known as calcium diicoanoate), magnesium stearate, and mixtures thereof; preferably stearic acid, aluminium stearate, calcium arachidate and magnesium stearate; most preferred is magnesium stearate. The concentration range of the lubricant is from about 5 to 15 mg per tablet. Preferred concentrations of the lubricant include, but are not limited to, 5 to 10 mg, 5 to 9 mg, 5 to 8 mg, 6 to 10 mg, 6 to 9, 6 to 8 mg, 7 to 10 mg, 7 to 9 mg, 7 to 8 mg per tablet or 8 mg per tablet, of which the 8 mg per tablet concentration is especially preferred in the tablet containing 1 mg meloxicam.

Another preferred concentration range of the lubricant is selected from the group consisting of 8 to 15 mg, 8 to 14 mg, 8 to 13 mg, 8 to 12 mg, 9 to 15 mg, 9 to 14 mg, 9 to 13 mg, 9 to 12 mg, 10 to 15 mg, 10 to 14 mg, 10 to 13 mg, 10 to 12 mg, 11 to 15 mg, 11 to 14 mg, 11 to 13 mg, 11 to 12 mg per tablet or 12 mg per tablet, of which the 12 mg concentration is especially preferred in the tablet containing 2.5 mg meloxicam per tablet.

Flavoring may also be included in the tablet of the invention. The flavor may be any pharmaceutically or veterinarally acceptable flavor, whether natural or artificial. The flavor is preferably an artificial beef flavor with a concentration range from about 40 to 160 mg per tablet. Preferred concentrations of the flavor include 40 to 100 mg, 50 to 100 mg, 60 to 100 mg, 70 to 100 mg, or 80 to 100 mg per tablet; with about 80 mg per tablet being especially preferred in the tablet containing 1 mg meloxicam.

Other preferred concentration ranges of the flavor are from about 90 to 160 mg, 100 to 150 mg, 110 to 140 mg, 110 to 130 mg per tablet or 120 mg per tablet; with about 120 mg per tablet being especially preferred in the tablet containing 2.5 mg meloxicam per tablet.

According to the invention, the tablet contains 0.5 to 5 mg of meloxicam and has a tablet weight of 500 mg to 2000 mg. Preferably, the tablet contains 0.5 mg to 5 mg of meloxicam and has a total tablet weight of 500 mg to 2000 mg with a tablet diameter ranging from 10 mm to 20 mm. Additionally, the tablet has a height preferably ranging from 3 mm to 8 mm, more preferably 4 mm to 8 mm, 5.3 mm to 7.3 mm or 4.5 mm to 6.5 mm, even more preferred 5 mm, 5.5 mm or 6.3 mm.

The preferred amount of meloxicam per tablet is from 1 mg to 4 mg, more preferred from 1 mg to 3 mg or 1.5 mg to 2.5, even more preferred is 1 mg and 2.5 mg. The tablet has a total weight in the range from 500 to 2000 mg, preferably from 700 to 1500 mg, most preferred 800 mg and 1200 mg. In a preferred embodiment, the tablet containing 0.5 mg to 1.8 mg meloxicam has a total weight of about 500 mg to 900 mg and a diameter ranging from 10 to 15 mm. Even more preferred is a tablet containing 0.5 mg to 1.8 mg meloxicam with a total weight of about 500 mg to 900 mg, a diameter ranging from 10 mm to 15 mm and a height ranging from 4.5 mm to 6.5 mm.

In another preferred embodiment the tablet containing 1.9 to 5 mg meloxicam has a total weight of 900 to 2000 mg and a diameter of 15 mm to 20 mm. Even more preferred is a tablet containing 1.9 to 5 mg meloxicam with a height of 900 mg to 2000 mg, a diameter of 15 mm to 20 mm and a thickness ranging from 5.3 mm to 7.3 mm. In an especially preferred embodiment of the invention, the tablet contains 1 mg meloxicam homogenously dispersed in a total tablet weight of 800 mg or 2.5 mg meloxicam in a tablet with a total weight of 1200 mg.

The flavor contributes 2 to 15% of the total weight of the tablet. According to the invention the tablet most preferably contains 1 mg meloxicam per 800 mg tablet and the flavor content is about 10% by weight per tablet or the tablet contains 2.5 mg meloxicam per tablet with a total weight of 1200 mg with a flavor content of about10% by weight per tablet.

Figure 1B:
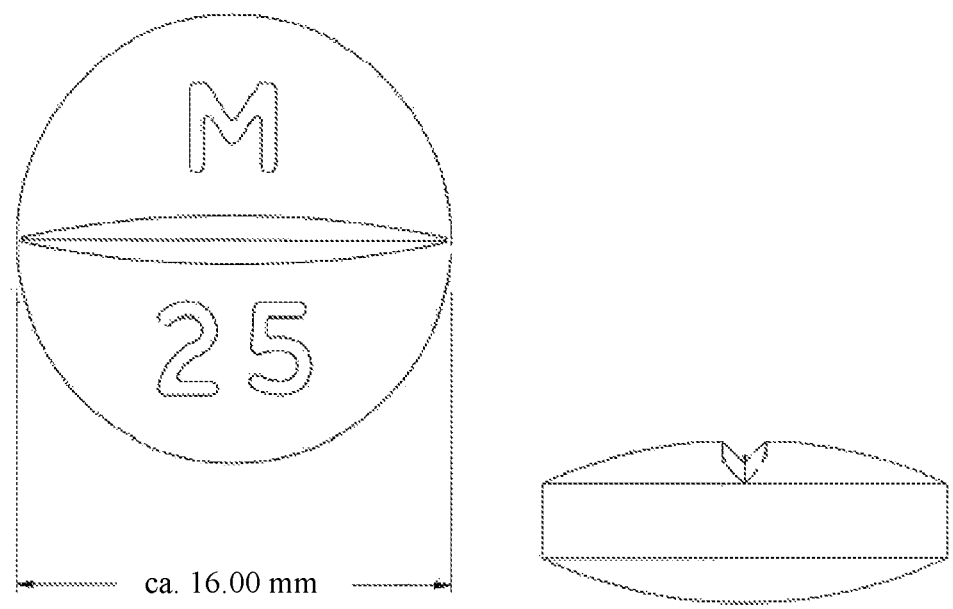
FIG. 1B: Tablet shape and dimensions of 2.5 mg meloxicam tablets.
Figure 2:
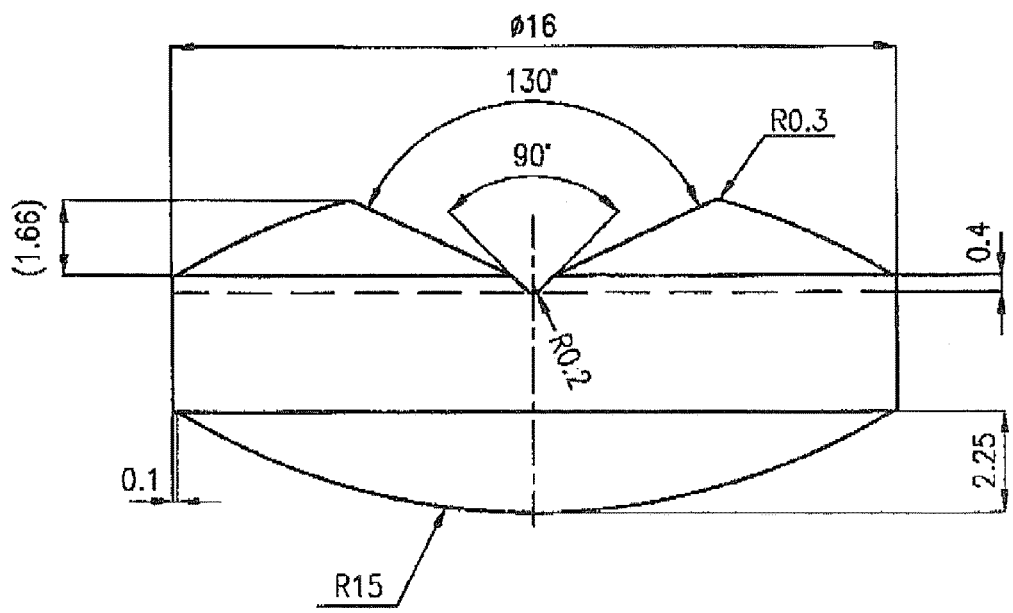
FIG. 2: Tablet shape and breaking notch including dimensions.
Figure 2:
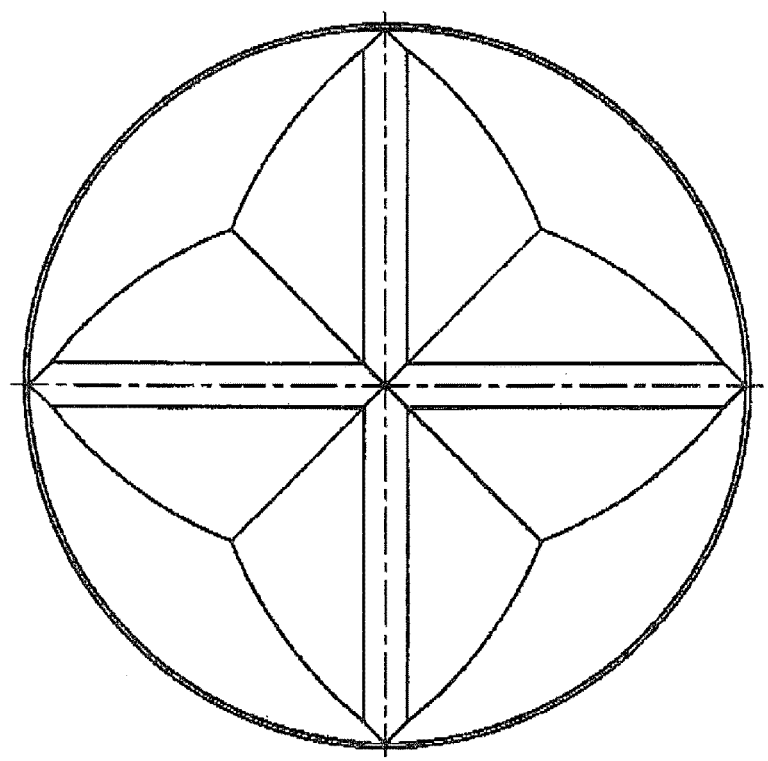

According to another aspect the tablet has a shape as shown, for example in FIGS. 1A, 1B, and FIG. 2. Generally, the tablet contains 0.5 mg to 5 mg of meloxicam and has a total tablet weight of 500 mg to 2000 mg. The dimensions of the tablet are given by its diameter, which ranges from 10 mm to 20 mm, and its height ranging from 3 mm to 8 mm. Preferably the tablet containing 1 mg meloxicam has a total weight of 500 mg to 900 mg, a diameter ranging from 10 mm to 20 mm, 11 mm to 18 mm, 12 mm to 17 mm, 13 mm to 16 mm, or 14 mm to 15 mm.

An alternative preferred range is from 12 mm to 15mm; and a height ranging from 4 mm to 8 mm, 5 mm to 7 mm, 5 mm to 6 mm, preferably 5 mm to 6 mm. Especially preferred is a tablet, as shown in FIG. 1A, that contains meloxicam in a concentration of 1.0 mg per tablet with a total weight of 800 mg, a diameter of 14 mm and a height of 5.5 mm. Preferably, the tablet containing 2.5 mg meloxicam has a total weight of 900 to 2000 mg, a diameter ranging from 10 mm to 20 mm, 11 mm to 18 mm, 12 mm to 17 mm, 13 mm to 16 mm, or 14 mm to 15 mm.

An alternative preferred range is from 15 mm to 18 mm or 15 mm to 17 mm; and a height ranging from 4 mm to 8 mm, 5 mm to 7 mm, or 5 mm to 6 mm. An alternative preferred range is from 5 mm to 8 mm. Especially preferred is a tablet, as shown in FIG. 1B, containing meloxicam in a concentration of 2.5 mg per tablet with a total weight of 1200 mg, a diameter of 16 mm and a height of 6.3 mm.

As shown in FIGS. 1A and 1B, the tablet has a breaking notch/score line that enables the tablet to be broken into two units resulting in two units containing an equal amount of meloxicam due to its homogenous distribution within the tablet.

According to another aspect of the invention, the tablet has two breaking notches/score lines that are perpendicular to one another as shown in FIG. 2. Thus, the tablet can be quartered resulting into either four or two units of equal amount of meloxicam, which is only possible because of the homogenous distribution of meloxicam in the tablet.

The solid formulation according to the invention is a directly compressed tablet without any granulation step. The active ingredient in the solid formulation is preferably meloxicam as a free base.

In contrast to the state of the art, the tablet according to the invention is produced by compressing a powder directly into a tablet resulting in a low content of the active ingredient meloxicam. Additionally, the tablet has a large size which is desirable as it makes it easier for the animal to pick up the tablet. Additionally, the size was also important to make it easier to divide the tablet in order to achieve a precise administration of the drug, especially in the case of a low dose application. For example, as described above, the tablet containing 1 mg of meloxicam has a diameter of 14 mm, whilst the tablet containing 2.5 mg meloxicam has a diameter of 16 mm.

As previously described, the concentration of the active pharmaceutical ingredient is low and is considered to be in a critical phase. The concentration of meloxicam is in a concentration range that makes it difficult to produce a large tablet with a uniform distribution of the active ingredient within tablet.

Surprisingly, it has been found that the production method of this invention enables a uniform distribution of meloxicam despite the low concentration of the active ingredient. This enables the production of a tablet that can be divided as described with an ensured precise administration. As described above, the tablet of the present invention is preferably marked with a breaking notch/score line that enables the user to break the tablet more easily into two, three or four pieces. The direct compression process comprises the following steps:

1) Mixing meloxicam with 10-50% of a filler/disintegrant, preferably 20 to 40%, more preferred 25-35%, even more preferred is 33%; followed by screening through suitable a mesh that has a mesh size of 0.6 to 1.5 mm, preferably 0.7 to 1.4 mm, more preferred 0.8 to 1.3 mm, even more preferred is a mesh size selected from 0.6 mm, 0.8 mm, 1.0 mm or 1.5 mm.
2) Mixing a pH adjuster and one or more optional coloring agents, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
3) Mixing of 90-50% of a filler/disintegrant, preferably 60 to 80%, more preferred 60-70%, and even more preferred is about 67%; and optionally a second filler/disintegrant, flow regulator, lubricant and/or artificial flavor may be added, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
4) Admixing the mixtures or materials obtained in steps 1) and 2) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
5) Final blending of the mixtures obtained in steps 3) and 4) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.mm or 1.5 mm.
6) Compression of the powder mixture obtained in step 5) into a tablet.

The direct compression process comprises preferably the following steps:
1) Mixing meloxicam with 10-50% of a filler/disintegrant, preferably 20 to 40%, more preferred 25-35%, even more preferred is 33% of filler/disintegrant, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
2) Mixing of a pH adjuster and optional colorant, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
3) Mixing of 90-50% of the filler/disintegrant, preferably 60 to 80%, more preferred 60-70%, even more preferred is 67% of optionally a second filler/disintegrant, lubricant, and flavor, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
4) Admixing the blends, mixtures or materials obtained in steps 1) and 2) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
5) Final blending of the mixture obtained in steps 3) and 4) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm and 1.5 mm.
6) Compression of the powder mixture obtained in 5) into a tablet.

Thus, a solid tablet comprising meloxicam or a pharmaceutically acceptable salt thereof is provided, where the solid tablet is obtainable by the direct compression process comprising the steps 1 to 6 as described above.

In another embodiment, a solid tablet comprising meloxicam or a pharmaceutically acceptable salt thereof as described herein is provided, where the production of the solid tablet comprises one or more of the process steps 1 to 6 as described above. For example, the production process may comprise step 1, steps 1 and 4, steps 1, 4 and 6 or steps 1, 4, 5 and 6. However, the preferred method comprises steps 1 to 6.

Example: Method of Production

The following description of the production method is just one example and as such should not be understood as limiting.

The first step in the manufacturing process is the premixing of the active ingredient such as meloxicam or a pharmaceutically active salt thereof with a portion of filler/disintegrant such as starch, followed by mesh screening. Due to the low total amount of meloxicam or the pharmaceutically acceptable salt thereof in the tablet mixture, subsequent mixing with, for example about 900 revolutions, is necessary after addition of another screened mixture containing a pH adjuster such as sodium citrate and the option colorants (e.g., ferric oxides) to ensure a homogeneous distribution of the active ingredient in the matrix. Finally, a mixture of screened microcrystalline cellulose, meat flavor, the remaining amount of starch, colloidal silica anhydrous and magnesium stearate is added, followed by a final blending with, for example about 350 revolutions of the mixing container. The final blend is directly compressed into tablets.

EXAMPLES

I. Composition for a tablet with a total weight of 800 mg comprising 1 mg meloxicam and 10% flavor.

| Ingredients | mg/tablet |
| --- | --- |
| Meloxicam | 1.0 |
| Sodium Citrate Dihydrate | 65.6 |
| Maize Starch | 235.0 |
| Ferric Oxide Brown | 3.2 |
| Ferric Oxide Yellow | 3.2 |
| Microcrystalline Cellulose | 400.0 |
| Artificial Powdered Beef Flavor | 80.0 |
| Anhydrous Silicon Dioxide | 4.0 |
| Magnesium Stearate | 8.0 |
| Total | 800.0 |

II. Composition for a tablet with a total weight of 1200 mg comprising 2.5 mg meloxicam and 10% flavor.

| Ingredients | mg/tablet |
| --- | --- |
| Meloxicam | 2.5 |
| Sodium Citrate Dihydrate | 98.4 |
| Maize Starch | 351.5 |
| Ferric Oxide Brown | 4.8 |
| Ferric Oxide Yellow | 4.8 |
| Microcrystalline Cellulose | 600.0 |
| Artificial Powdered Beef Flavor | 120.0 |
| Anhydrous Silicon Dioxide | 6.0 |
| Magnesium Stearate | 12.0 |
| Total | 1200.0 |

What is claimed:

1. A method of treating an animal, comprising administering at least a portion of a solid tablet to the animal, wherein the tablet comprises meloxicam or a pharmaceutically acceptable salt thereof and at least one excipient, the tablet comprises about 0.5 to 5 mg of meloxicam, the tablet has a total tablet weight of about 500 mg to 2000 mg, and a weight ratio of meloxicam to tablet is no greater than 0.21%.

2. The method of claim 1, wherein meloxicam is homogenously dispersed within the tablet, the tablet comprising a maximum dosage, and the tablet comprises a score line to enable selection of a portion of the tablet having a dosage smaller than the maximum dosage, and the method further comprising:

selecting a dosage smaller than the maximum dosage by separating a tablet portion at the at least one score line from the tablet; and
administering the tablet portion to the animal.

3. The method of claim 2, wherein:
the selected dosage is one half of the maximum dosage; and
the tablet portion is one half of the tablet.

4. The method of claim 2, wherein:
the selected dosage is one fourth of the maximum dosage; and
the tablet portion is one fourth of the tablet.

5. The method of claim 1, wherein the animal is a feline or a canine.

6. The method of claim 1, wherein the animal is a canine suffering from a musculoskeletal disorder.

7. The method of claim 1, wherein the tablet is directly-compressed of powder, and the powder consists of particles possessing a particle size of 600 µm to 1500 µm.

8. The method of claim 7, wherein the powder further comprises particles possessing a particle size of less than 600 µm.

9. The method of claim 1, wherein the tablet further comprises an artificial or natural flavor.

10. The method of claim 9, wherein the flavor is present in an amount of about 2 to 15% by weight of the total tablet weight.

11. The method of claim 9, wherein the flavor is an artificial beef flavor.

12. The method of claim 1, wherein the tablet comprises meloxicam as a free base.

13. The method of claim 1, wherein the excipient comprises a filler selected from the group consisting of sodium carboxymethyl cellulose.

14. The method of claim 1, wherein the at least one excipient comprises a pH adjuster selected from the group consisting of tartaric acid, maleic acid, and mixtures thereof.

15. The method of claim 1, wherein the tablet:
contains meloxicam in a concentration of 1 mg per tablet;
possesses a height of from 5 mm to 7 mm;
possesses a diameter of from 11 mm to 18 mm; and
possesses a total weight of 500 mg to 900 mg.

16. The method of claim 1, wherein the tablet:
contains meloxicam in a concentration of 2.5 mg per tablet;
possesses a height of from 5 mm to 8 mm;
possesses a diameter of from 11 mm to 18 mm; and
possesses a total weight of from 900 mg to 2000 mg.

17. The method of claim 1, wherein the weight ratio of meloxicam to tablet is no greater than 0.125%.

* * * * *